United States Patent
Liu et al.

(10) Patent No.: US 9,471,748 B2
(45) Date of Patent: Oct. 18, 2016

(54) METHOD FOR SHARING MEDICAL IMAGE DATA BASED ON CLOUD PLATFORM, CLOUD PLATFORM AND SYSTEM

(71) Applicant: Shenyang Neusoft Medical Systems Co., Ltd., Shenyang (CN)

(72) Inventors: Jiren Liu, Shenyang (CN); Shuangxue Li, Shenyang (CN); Shanshan Lou, Shenyang (CN); Jun Yu, Shenyang (CN); Jinjun Liu, Shenyang (CN); Huiyang Li, Shenyang (CN)

(73) Assignee: Shenyang Neusoft Medical Systems Co., Ltd., Shenyang (CN)

( * ) Notice: Subject to any disclaimer, the term of this patent is extended or adjusted under 35 U.S.C. 154(b) by 499 days.

(21) Appl. No.: 13/954,984

(22) Filed: Jul. 31, 2013

(65) Prior Publication Data
US 2014/0350953 A1   Nov. 27, 2014

(30) Foreign Application Priority Data

May 27, 2013   (CN) .......................... 2013 1 0202724

(51) Int. Cl.
   *G06K 9/00*   (2006.01)
   *G06F 19/00*   (2011.01)
   *A61M 5/00*   (2006.01)

(52) U.S. Cl.
   CPC ............ *G06F 19/321* (2013.01); *A61M 5/007* (2013.01)

(58) Field of Classification Search
   CPC .......................... G06F 19/321; A61M 5/007
   See application file for complete search history.

(56) References Cited

U.S. PATENT DOCUMENTS

| 8,170,315 | B2 * | 5/2012 | Mistretta ............... G06T 11/006 |
| | | | 382/131 |
| 2008/0006282 | A1 | 1/2008 | Sukovic et al. |
| 2010/0030073 | A1 | 2/2010 | Kalafut |
| 2011/0034801 | A1 | 2/2011 | Baumgart |
| 2013/0208966 | A1 * | 8/2013 | Zhao ..................... G06F 9/5072 |
| | | | 382/131 |

FOREIGN PATENT DOCUMENTS

| CN | 102831561 A | 12/2002 |
| CN | 102904953 A | 1/2013 |
| DE | 102011088160 B3 | 5/2013 |

OTHER PUBLICATIONS

Shini, S. G., Tony Thomas, and K. Chithraranjan. "Cloud based medical image exchange-security challenges." Procedia Engineering 38 (2012): 3454-3461.*

(Continued)

*Primary Examiner* — Shefali Goradia
(74) *Attorney, Agent, or Firm* — Kilpatrick Townsend & Stockton LLP (57) ABSTRACT

A method for sharing medical image data based on a cloud platform, a cloud platform and a system are disclosed. The cloud platform is connected to at least one medical imaging device. The method includes: receiving a medical image and/or scan data transmitted from the at least one medical imaging device; and storing, on the cloud platform, the medical image and/or scan data from the at least one medical imaging device.

16 Claims, 6 Drawing Sheets

(56) References Cited

OTHER PUBLICATIONS

Yang, Chao-Tung, et al. "Implementation of a medical image file accessing system on cloud computing." Computational Science and Engineering (CSE), 2010 IEEE 13th International Conference on. IEEE, 2010.*

Li, Zhuo-Rong, et al. "A secure electronic medical record sharing mechanism in the cloud computing platform." Consumer Electronics (ISCE), 2011 IEEE 15th International Symposium on. IEEE, 2011.*

Ultrafast and scalable cone-beam CT reconstruction using MapReduce in a cloud computing environment. Medical Physics, vol. 38, 2011, S. 6603-6609.

* cited by examiner

METHOD FOR SHARING MEDICAL IMAGE DATA BASED ON CLOUD PLATFORM, CLOUD PLATFORM AND SYSTEM

FIELD OF THE INVENTION

The present invention relates to the field of embedded system, and in particular to a method for sharing medical image data based on a cloud platform, a cloud platform and a system.

BACKGROUND OF THE INVENTION

Currently, medical devices are apparatus, instruments, materials or other objects used alone or in combination on a user, and the medical devices also include necessary software. Medical imaging devices are medical devices for obtaining medical images by scanning users.

In an existing medical imaging device, for example a computed tomography (CT) scanner, the reconstruction and storage of the medical image is performed by the device itself. For example, customizing a scan plan for a user, scanning a user, storing scan data, reconstructing a medical image based on scan data, and diagnosing a medical image are all performed by the CT scanner itself. A certain CT scanner can not obtain scan data of other CT scanner and can not refer to scan data of other CT scanner during scanning.

It can be seen that data sharing between different medical imaging devices can not be achieved in the prior art.

SUMMARY OF THE INVENTION

One object of the invention is to provide a method for sharing medical image data based on a cloud platform, so as to solve the technical problem in the prior art that data sharing between different medical imaging devices can not be achieved.

Another object of the invention is to apply the above-mentioned conception to a specific application environment, therefore a cloud platform for sharing medical image data is provided, for ensuring implementation and application of the method.

In order to solve the above-mentioned technical solution, a method for sharing medical image data based on a cloud platform is provided according to an embodiment of the invention, the cloud platform is connected to at least one medical imaging device, and the method includes:

receiving a medical image and/or scan data transmitted from the at least one medical imaging device; and storing, on the cloud platform, the medical image and/or the scan data from the at least one medical imaging device.

Optionally, in a case that the scan data is transmitted from a current medical imaging device, the method further includes:

in response to a medical image generation request from the current medical imaging device, reconstructing a corresponding medical image based on the scan data from the current medical imaging device.

Optionally, the reconstructing a corresponding medical image based on the scan data from the current medical imaging device includes:

dividing the scan data from the current medical imaging device into multiple data sub-sets;

distributing the multiple data sub-sets to multiple compute nodes chosen according to a predetermined condition correspondingly, so as to trigger the multiple compute nodes to respectively calculate medical sub-images of the multiple data sub-sets, wherein the number of the data sub-sets consists with the number of the multiple compute nodes; and generating a medical image corresponding to the scan data by using the medical sub-images of the multiple data sub-sets.

Optionally, the method further includes:

returning the medical image to the current medical imaging device.

Optionally, the method further includes:

in response to a guide scan request from a current medical imaging device, performing a guide scan of the current medical imaging device based on a stored medical image and/or scan data from other medical imaging device.

Optionally, the medical imaging device includes a device capable of measuring cardiac output and a computed tomography CT scanner, and the performing a guide scan of the current medical imaging device includes:

in response to an operation of enhanced scan to be performed by a current CT scanner on an object to be scanned, acquiring, from the cloud platform, cardiac output of the object to be scanned which is obtained by using the device capable of measuring cardiac output;

calculating, based on the cardiac output, total amount and injection speed of contrast medium required by the enhanced scan to be performed on the object to be scanned; and transmitting the total amount and injection speed of the contrast medium to the current CT scanner, so the current CT scanner performs enhanced scan on the object to be scanned.

Optionally, the performing a guide scan of the current medical imaging device includes:

in response to a received medical image of a scanned portion of an object to be scanned which is transmitted from the current medical imaging device, performing matching on the cloud platform to obtain a stored medical image and/or scan data of a same scanned portion of other object; and generating, based on the medical image and/or the scan data obtained by the matching, a parameter required by dose optimization of the object to be scanned, so the current medical imaging device performs a dose-optimized scan on the object to be scanned base on the parameter.

Optionally, the medical image and/or the scan data includes: a first medical image and/or first scan data obtained by scanning a currently-scanned object by a first medical imaging device after a marked point of the currently-scanned object is predetermined; and the method further includes:

judging whether an object to be scanned which is scanned by a second medical imaging device is the currently-scanned object, and if it is, transmitting the first medical image and/or the first scan data to the second medical imaging device, so the second medical imaging device fuses the first medical image and/or the first scan data and a second medical image and/or second scan data obtained by scanning of the second medical imaging device.

Optionally, the method further includes: during the receiving a medical image and/or scan data transmitted from the at least one medical imaging device, receiving a permission setting parameter corresponding to the medical image and/or the scan data, wherein the permission setting parameter indicates access permission of the medical image and/or the scan data;

and the method further includes: after the storing, on the cloud platform, the medical image and/or the scan data from the at least one medical imaging device, in response to a request of acquiring a medical image and/or scan data of a scanned to object which is transmitted by an electronic device, judging whether there is an access permission based on the permission setting parameter of the medical image and/or the scan data, and if it is, returning the medical image and/or the scan data.

Correspondingly, a cloud platform for sharing medical image data is further provided according to an embodiment of the invention, the cloud platform is connected to at least one medical imaging device, and the cloud platform includes:

a first receiving module adapted for receiving a medical image and/or scan data transmitted from the at least one medical imaging device; and a storage module adapted for storing, on the cloud platform, the medical image and/or the scan data from the at least one medical imaging device.

Optionally, the cloud platform further includes:

a reconstruction module adapted for, in response to a medical image generation request from a current medical imaging device, reconstructing a corresponding medical image based on the scan data from the current medical imaging device.

Optionally, the reconstruction module includes:

a dividing sub-module adapted for dividing the scan data from the current medical imaging device into multiple data sub-sets;

a distributing sub-module adapted for distributing the multiple data sub-sets to multiple compute nodes chosen according to a predetermined condition correspondingly, so as to trigger the multiple compute nodes to respectively calculate medical sub-images of the multiple data sub-sets, wherein the number of the data sub-sets consists with the number of the multiple compute nodes; and a generation sub-module adapted for generating a medical image corresponding to the scan data by using the medical sub-images of the multiple data sub-sets.

Optionally, the cloud platform further includes:

a first returning module adapted for returning the medical image to the current medical imaging device.

Optionally, the cloud platform further includes:

a guide scan module adapted for, in response to a guide scan request from a current medical imaging device, performing a guide scan of the current medical imaging device based on a stored medical image and/or scan data from other medical imaging device.

Optionally, the medical imaging device includes a device capable of measuring cardiac output and a computed tomography CT scanner, and the guide scan module includes:

an acquiring sub-module adapted for, in response to an operation of enhanced scan to be performed by a current CT scanner on an object to be scanned, acquiring, from the cloud platform, cardiac output of the object to be scanned which is obtained by using the device capable of measuring cardiac output;

a calculating sub-module adapted for calculating, based on the cardiac output, total amount and injection speed of contrast medium required by the enhanced scan to be performed on the object to be scanned; and a transmitting sub-module adapted for transmitting the total amount and injection speed of the contrast medium to the current CT scanner, so the current CT scanner performs enhanced scan on the object to be scanned.

Optionally, the guide scan module includes:

a matching sub-module adapted for, in response to a received medical image of a scanned portion of an object to be scanned which is transmitted from the current medical imaging device, performing matching on the cloud platform to obtain a stored medical image and/or scan data of a same scanned portion of other object; and a dose modulation sub-module adapted for generating, based on the medical image and/or the scan data obtained by the matching, a parameter required by dose optimization of the object to be scanned, so the current medical imaging device performs a dose-optimized scan on the object to be scanned base on the parameter.

Optionally, the medical image and/or the scan data comprises: a first medical image and/or first scan data obtained by scanning a currently-scanned object by a first medical imaging device after a marked point of the currently-scanned object is predetermined; and the cloud platform further includes:

a first judging module adapted for judging whether an object to be scanned which is scanned by a second medical imaging device is the currently-scanned object, and a transmitting module adapted for transmitting the first medical image and/or the first scan data to the second medical imaging device if the first judging module determines that the object to be scanned which is scanned by the second medical imaging device is the currently-scanned object, so the second medical imaging device fuses the first medical image and/or the first scan data and a second medical image and/or second scan data obtained by scanning of the second medical imaging device.

Optionally, the cloud platform further includes:

a second receiving module adapted for receiving a permission setting parameter corresponding to the medical image and/or the scan data, wherein the permission setting parameter indicates access permission of the medical image and/or the scan data;

a second judging module adapted for, in response to a request of acquiring a medical image and/or scan data of a scanned object which is transmitted by an electronic device, judging whether there is an access permission based on the permission setting parameter of the medical image and/or the scan data; and a second returning module adapted for returning the medical image and/or the scan data if the second judging module determines that there is an access permission.

A system for sharing data is further provided according to an embodiment of the invention, the system includes a cloud platform and at least one medical imaging device connected to the cloud platform, wherein the cloud platform includes:

a first receiving module adapted for receiving a medical image and/or scan data transmitted from the at least one medical imaging device; and a storage module adapted for storing, on the cloud platform, the medical image and/or the scan data from the at least one medical imaging device.

It can be seen from the above-mentioned technical solution that, in the embodiments of the invention, the cloud platform is connected to at least one medical imaging device and may receive a medical image and/or scan data transmitted from the at least one medical imaging device, the medical image and/or the scan data from the at least one medical imaging device is stored on the cloud platform directly. The medical image and/or the scan data are stored on the cloud platform, so each medical imaging device may acquire the medical image and/or scan data of other medical imaging device via the cloud platform. Thereby, the medical image data sharing between the at least one medical imaging device is achieved.

Based on the above-mentioned solution, in a case that scan data of each medical imaging device is stored on the cloud platform, the process to reconstruct the medical image is the process to generate the medical image according to the scan data for each medical imaging device, the reconstruction of the medical image may also be implemented on the cloud platform side. Thereby, the efficiency of the medical image reconstruction is improved and the resource of the medical imaging device itself may be saved.

Moreover, each medical imaging device, during scanning the medical image, may acquire, from the cloud platform, the medical image and/or scan data obtained by scanning of other medical imaging device for reference. Thereby, the quality of the medical image and the accuracy of the diagnosis are improved.

Furthermore, each medical imaging device, during performing dose modulation with respect to a certain portion of an object to be scanned, may refer to the scan result of the same portion of the object to be scanned from other medical imaging device, so as to determine a modulation parameter for the current scan of the object to be scanned. Thereby, the scan data and/or the medical image are more accurate.

Furthermore, the medical image data sharing achieved based on the cloud platform may support fusion of medical images and/or scan data obtained from different types of medical imaging devices (for example, CT scanner and PET).

Furthermore, for the medical image and/or scan data sharing achieved based on the cloud platform, a corresponding permission of the medical image and/or scan data of each user scanned by each medical imaging device may be set, and only an object that has the access permission can obtain the medical image and/or scan data of other object. Thereby, the security of the medical image and/or scan data may be improved.

BRIEF DESCRIPTION OF THE DRAWINGS

Technical solutions of the embodiments of the present applicant and/or the prior art will be illustrated more clearly with the following brief description of the drawings. Apparently, the drawings described below constitute only some embodiments of the invention. Those skilled in the art may obtain some other drawings from these drawings without any creative work.

DETAILED DESCRIPTION OF THE INVENTION

In order to make those skilled in the art better understand the solutions of the invention, the technical solutions according to the embodiments of the present invention will be described clearly and completely as follows in conjunction with the drawings. It is obvious that the described embodiments are only part but not all of embodiments of the present invention. Other embodiments obtained by those skilled in the art based on the embodiments in the present invention without any creative work fall within the protection scope of the present invention.

Figure 1:
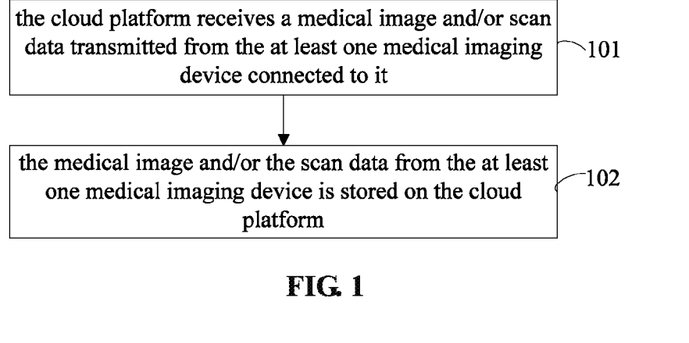
FIG. 1 is a flowchart of a first embodiment of a method according to the invention.

Referring to FIG. 1, a flowchart of a first embodiment of a method for sharing medical image data based on a cloud platform according to the invention is shown. The cloud platform is connected to at least one medical imaging device. The embodiment includes the following steps.

Step 101: The cloud platform receives a medical image and/or scan data transmitted from the at least one medical imaging device.

In this embodiment, the cloud platform may be in communication connection with one or more medical imaging device via a network, so that the medical image and/or scan data may be transmitted between the cloud platform and the medical imaging device. Generally, in a case that there are multiple medical imaging devices, the multiple medical imaging devices may be devices in a same hospital or in different hospitals. The medical imaging device is a medical device which can perform scanning and which needs to implement the medical image and/or scan data sharing. For example, a CT scanner, an MRI (Magnetic Resonance Imaging) device, a ultrasound equipment, an X-ray apparatus, a PET (Positron Emission Computed Tomography)-CT all belong to the medical imaging device of the application.

Each medical imaging device may transmit scan data, i.e., raw data based on which a corresponding medical image is calculated, obtained by scanning an object to be scanned. Alternatively, each medical imaging device may transmit a medical image reconstructed by the medical imaging device based on the scan data.

Step 102: The medical image and/or the scan data from the at least one medical imaging device is stored on the cloud platform.

The cloud platform may provide a dedicated storage space to store the medical image and/or scan data from one or more medical imaging devices connected to the cloud platform.

In the present embodiment, each medical imaging device no longer stores the scan data and/or medical image in its own storage space. Instead, each medical imaging device transmits the scan data and/or the medical image to the cloud platform connected to it, and the cloud platform stores the medical image and/or scan data of all the medical imaging devices connected to it. In this way, a certain medical imaging device, when needing to acquire a medical image and/or scan data of other medical imaging device, may directly read the medical image and/or scan data from the cloud platform connected to it. Thereby, the medical image and/or scan data sharing between all the medical imaging devices connected to the cloud platform is achieved.

Figure 2:
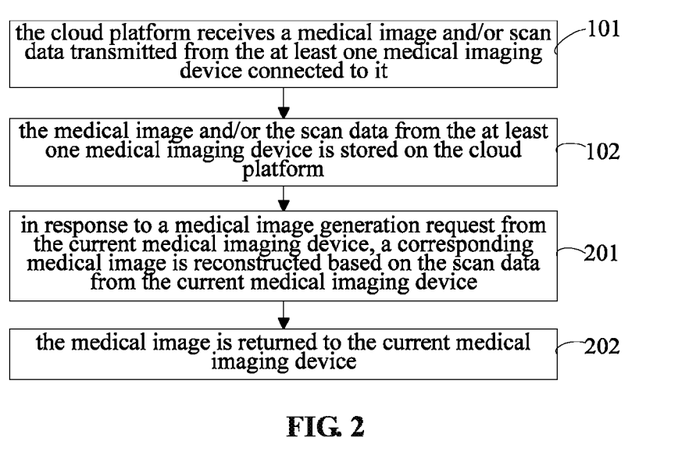
FIG. 2 is a flowchart of a second embodiment of the method according to the invention.

Referring to FIG. 2, a flowchart of a second embodiment of the method for sharing medical image data based on a cloud platform according to the invention is shown. If the current medical imaging device transmits scan data to the cloud platform, the embodiment further includes the following step after Step 102 in which the medical image and/or scan data sharing between all the medical imaging devices connected to the cloud platform is achieved.

Step 201: in response to a medical image generation request from the current medical imaging device, a corresponding medical image is reconstructed based on the scan data from the current medical imaging device.

Since the current medical imaging device transmits the scan data to the cloud platform, the reconstruction of the medical image of the scan data may be implemented on the cloud platform side. The current medical imaging device may transmit a medical image generation request to the cloud platform, then the cloud platform reconstructs, based on the stored scan data from the current medical imaging device, the medical image corresponding to the scan data.

In a different embodiment, the cloud platform may include multiple compute nodes. One compute node may be implemented by one computer. Then the cloud platform may distribute different scan data obtained by the scanning of different medical imaging devices to different compute nodes respectively. Alternatively, the cloud platform may divide the scan data obtained by the scanning of a same medical imaging device into multiple sub-tasks and distribute the multiple sub-tasks to different compute nodes respectively.

Figure 3:
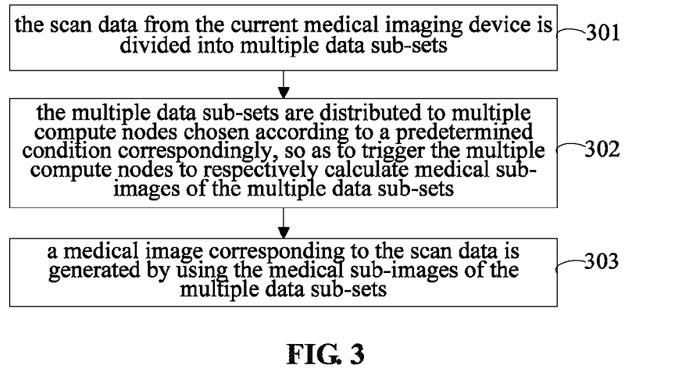
FIG. 3 is a flowchart of Step 201 in the second embodiment of the method according to the invention.

Referring to FIG. 3, in a case that the scan data obtained by the scanning of the same medical imaging device is divided into multiple sub-tasks and the multiple sub-tasks are distributed to different compute nodes, Step 201 may include the following steps.

Step 301: the scan data from the current medical imaging device is divided into multiple data sub-sets.

Firstly, the cloud platform divides the scan data from the current medical imaging device into multiple data sub-sets. For example, as for an iterative method, the minimum value is needed to be solved as shown in Equation (1), and the obtained x is the pixel values of the medical image:

$$x = \underset{x}{\operatorname{argmin}}\left\{\frac{1}{2}(y - Ax)^T D(y - Ax) + U(x)\right\} \quad (1)$$

In Equation (1), A is an orthographic projection matrix, D is a confidence diagonal matrix, U (x) is a regularization term, and y is a projection value. U (x) may be, for example, as shown in Equation (2):

$$U(x) = \frac{1}{p\sigma^p} \sum_k \sum_{j \in C_k} b_{j,k} \rho(x_j - x_k), \quad (2)$$

where $$\rho(\Delta) = \frac{|\Delta|^p}{1 + |\Delta/c|^{p-q}}$$

In Equation (2), p, q and c are parameters for controlling image quality, and generally 2≥p≥q≥1; c and σ are empirical parameters, where σ is a ratio between a control regularization term and a primary item, c is a boundary reservation feature of the control regularization term function, the larger c is, the brighter boundary of the image reserves, and c and σ may be set by the skilled in the art independently; $b_{jk}$ is a weighted value, which is the normalized reciprocal of the distance between the pixel $x_j$ and the pixel $x_k$; and $C_k$ is a set of indexes of neighborhood points of the pixel point $x_k$, such as eight neighborhood.

Typical values of parameters p, q, c and σ may be p=2.0, q=1.2, c=10, σ=0.01.

Solving the minimum value in Equation (1) is converted into making the derivative of $x_j$ equal to zero. Therefore, solving the minimum value in Equation (1) is converted into the iterative method as follows.

It is assumed that $x^{(0)}$ is 0, and n=0. Step a): for arbitrary pixel point j in the image, $x_j$ in the following Equation (3) is solved:

$$\theta_{1,j} + (x_j^{(n)} - x_j)\theta_{2,j} - \frac{1}{p\sigma^p} \sum_{\{j,k\} \in C} b_{j,k} I(x_j - x_k^{(n)}) = 0 \quad (3)$$

where $$I(\Delta) = \frac{|\Delta|^{p-1}}{1 + |\Delta/c|^{p-q}}\left(p - \left(\frac{p-q}{c^{p-q}}\right)\frac{|\Delta|^{p-q}}{1 + |\Delta/c|^{p-q}}\right)\operatorname{sign}(\Delta)$$

$$\theta_{1,j} = \sum_{i=1}^N d_i A_{ij}(y_i - A_{i*}x^{(n)})$$

$$= (A^T)_{j*}D(y - Ax^{(n)})$$

$$\theta_{2,j} = \sum_{i=1}^N d_i A_{ij}^2$$

Step b): all of the obtained $x_j$ compose $x^{(n+1)}$, let n=n+1, and then it is judged whether a convergence condition is met. Generally, the convergence condition is to judge whether the maximum difference between two solutions is less than a preset threshold value (for example, the threshold value may be 1). Alternatively, the control may be performed according to the number of times of the iterations, for example the number of times of the iterations n is greater than 1000. If the convergence condition is not met, the process returns to Step b); and if the convergence condition is met, the iterative process ends.

According to this embodiment, the medical image calculated in iteration steps of the Steps a-b is divided into several blocks. The iterations for the several blocks are performed respectively by the resources of the different compute nodes located on the cloud platform. After a certain number of times (for example, 5 times) of iterations, the results of all the compute nodes are synchronized. Then the block iterations continue, until the medical image converges or a certain number of times (for example, 500 times) of iterations is reached.

As for the iterative steps of Steps a-b, it is still assumed that $x^{(0)}$ is 0, and n=0. The medical image is firstly divided into several disjoint sets $\Omega_i$, where i=1 . . . N, and N is consistent with the number of subsequently-selected compute nodes.

Step 302: the multiple data sub-sets are distributed correspondingly to multiple compute nodes chosen according to a predetermined condition, so as to trigger the multiple compute nodes to respectively calculate medical sub-images of the multiple data sub-sets, where the number of the data sub-sets consists with the number of the multiple compute nodes.

The cloud platform distributes the multiple divided data sub-sets to multiple compute nodes chosen according to a predetermined condition correspondingly, and each of the multiple compute nodes calculates a medical sub-images of a corresponding data sub-set.

As for the above-mentioned example, the following calculation steps may be performed by the compute node i.

Step 1): assume that $x^{i(0)}=x^{(n)}$, m=0;

Step 2): for any $j \in \Omega_i$ of the image, $x_j$ in Equation (4) is solved:

$$\theta_{1,j} + (x_j^{i(m)} - x_j)\theta_{2,j} - \frac{1}{p\sigma^p} \sum_{\{j,k\} \in C} b_{j,k} I(x_j - x_k^{j(m)}) = 0 \qquad (4)$$

where $$I(\Delta) = \frac{|\Delta|^{p-1}}{1 + |\Delta/c|^{p-q}} \left( p - \left(\frac{p-q}{c^{p-q}}\right) \frac{|\Delta|^{p-q}}{1 + |\Delta/c|^{p-q}} \right) \text{sign}(\Delta)$$

$$\theta_{1,j} = \sum_{i=1}^{N} d_i A_{ij}(y_i - A_{i*}x^{(m)})$$
$$= (A^T)_{j*} D(y - Ax^{i(m)})$$

$$\theta_{2,j} = \sum_{i=1}^{N} d_i A_{ij}^2$$

Step 3): all of the obtained $x_j$ compose $x^{i(m+1)}$, let m=m+1, and then it is judged whether m reaches a predetermined number of times of iterations. If m dose not reach the predetermined number of times, the process returns to Step 2); and if m reaches the predetermined number of times, the iteration of the compute node i ends, and the result is represented by $x^i$, where $x^i$ is the medical sub-image computed by the ith compute node.

Step 303: a medical image corresponding to the scan data is generated by using the medical sub-images of the multiple data sub-sets.

The medical image corresponding to the scan data is generated by using the medical sub-images of the multiple data sub-sets. Specifically, after all the above-mentioned compute nodes finish their computation, the computation results $x^i$ of all the compute nodes are combined as $x^{(n+1)}$. Let n=n+1, and then it is judged whether a preset convergence condition is met. If the convergence condition is not met, the process returns to Step 1) for iteration; and if the convergence condition is met, the iterative process ends, and $x^{(n+1)}$ is the reconstructed medical image.

Next, returning to FIG. 2. Step 202, in which the medical image is returned to the current medical imaging device, may be performed on the cloud platform side after Step 201.

In the embodiment, the cloud platform may return a medical image to the current medical imaging device after reconstructing the medical image. The medical image may be provided as a scan result to a doctor or a patient for reference.

In the embodiment, for each medical imaging device, the medical image reconstruction may be performed by the cloud platform. Therefore, the use cost of the medical imaging device may be reduced, the efficiency of the medical image reconstruction may be improved and the resource of the medical imaging device itself may be saved.

Figure 4:
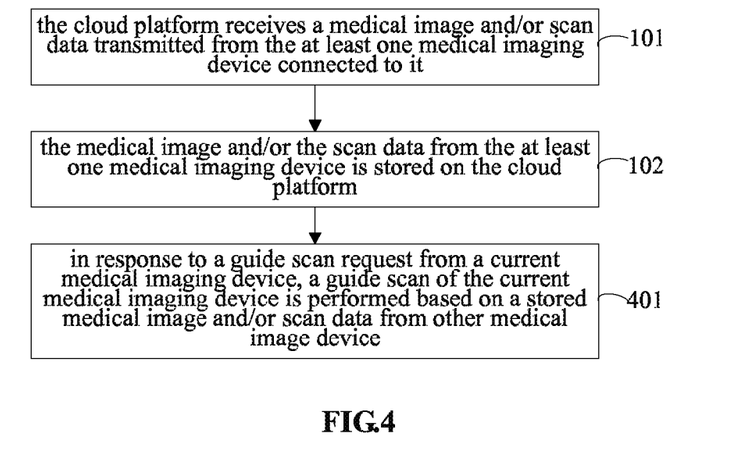
FIG. 4 is a flowchart of a third embodiment of the method according to the invention.

Referring to FIG. 4, a flowchart of a third embodiment of the method for sharing medical image data based on a cloud platform according to the invention is shown. In a practical application, the method may further include the following Step 401 after Steps 101-102 in the first embodiment of the method are performed.

Step 401: in response to a guide scan request from a current medical imaging device, a guide scan of the current medical imaging device is performed based on a stored medical image and/or scan data from other medical imaging device.

The medical image and/or scan data sharing between multiple medical imaging devices may be achieved based on the cloud platform. Therefore, if the current medical imaging device needs to perform a guide scan, for example the CT scanner needs to refer a medical image and/or scan data of other medical imaging device to perform an enhanced scan or a certain medical imaging device needs to perform dose optimization modulation before scanning, the guide scan may be triggered on the cloud platform, and the cloud platform implements the guide scan of the current medical imaging device based on the medical image and/or scan data of other medical imaging device stored on the cloud platform itself.

Figure 5:
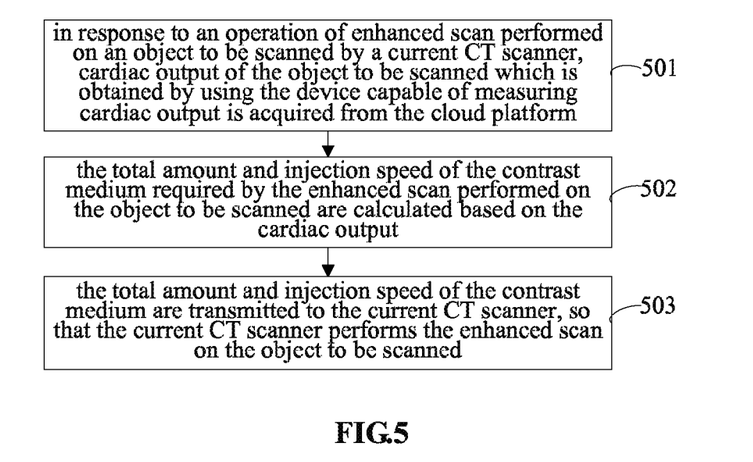
FIG. 5 is a flowchart of one example of the third embodiment of the method according to the invention.

In a specific application of the embodiment, it is assumed that the medical imaging device includes a device capable of measuring cardiac output and a CT scanner. Referring to FIG. 5, a flowchart of Step 401 is shown. The CT scanner needs to obtain the cardiac output by using the device capable of measuring cardiac output, to perform the enhanced scan. Thereby, total amount and injection speed of contrast medium required by the enhanced scan to be performed by the CT scanner may be calculated more accurately. Therefore, Step 401 may include the following steps.

Step 501: in response to an operation of enhanced scan to be performed by a current CT scanner on an object to be scanned, cardiac output of the object to be scanned which is obtained by using the device capable of measuring cardiac output is acquired from the cloud platform.

If the current CT scanner needs to perform the enhanced scan on the object to be scanned, the CT scanner transmits information of the object to be scanned and a trigger instruction to the platform. The cloud platform, after receiving the trigger instruction, may search for the cardiac output of the object to be scanned according to the information of the object to be scanned. The cardiac output of the object to be scanned is acquired by using the device capable of measuring cardiac output and is transmitted in advance to the cloud platform for storage.

It is assumed that the calculation model of the cardiac output is as shown in Equation (5):

$$V_T \frac{dC_T}{dt} = V \cdot (Q \cdot C_0 - C_T) \qquad (5)$$

V denotes the cardiac output. $C_T$ denotes the concentration of an organ to be scanned and may be set by the skilled in the art or a doctor independently. The concentration is usually chosen according to a scan protocol. For example, the concentration of a liver may be chosen as 200. $C_0$ denotes the injection concentration of the contrast medium. Q denotes the injection speed of the contrast medium. $V_T$ denotes blood volume of the scanned organ of the scanned object and may be obtained by a medical imaging device of the cloud platform or obtained by the model shown by Equation (6):

$$V_T = k*(0.25*(H/100)^3 + 0.063*W - 0.662) \quad (6)$$

H denotes the height of the object to be scanned. W denotes the weight of the object to be scanned. k denotes a proportional factor. Different organs to be scanned have different factors. For example, the factor of the heart is 0.07, and the factor of the lung is 0.09.

Step 502: the total amount and injection speed of the contrast medium required by the enhanced scan to be performed on the object to be scanned are calculated based on the cardiac output.

After the cloud platform finds out a matched cardiac output, the injection speed of the contrast medium Q may be calculated according to Equations (5) and (6) by referring to the required CT and the concentration of the contrast medium $C_0$. The total amount of the contrast medium may be obtained by multiplying the required scan time t by Q.

Step 503: the total amount and injection speed of the contrast medium are transmitted to the current CT scanner, so that the current CT scanner performs the enhanced scan on the object to be scanned.

The cloud platform, after obtaining the total amount and injection speed of the contrast medium, may transmit the total amount and injection speed of the contrast medium to the current CT scanner, to facilitate the optimization of the contrast medium injection plan for the current CT scanner, so as to perform the enhanced scan on the object to be scanned. In this specific application, the enhanced scan of the CT scanner is implemented by using the cardiac output obtained by scanning of other medical imaging device. The total amount and injection speed of the contrast medium is obtained by referring to the history result of the object to be scanned, and therefore the calculation result is more accurate.

Figure 6:
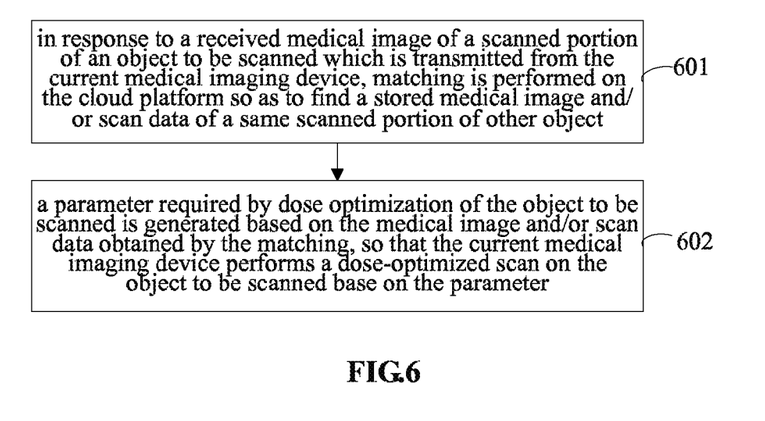
FIG. 6 is a flowchart of another example of the third embodiment of the method according to the invention.

In another specific application of the embodiment, a dose-optimized scan may be performed on a certain medical imaging device. Referring to FIG. 6, in a case that dose optimization is implemented for the guide scan of the current medical imaging device, the embodiment may include the following steps.

Step 601: in response to a received medical image of a scanned portion of an object to be scanned which is transmitted from the current medical imaging device, matching is performed on the cloud platform to find a stored medical image and/or scan data of a same scanned portion of other object.

In the embodiment, the case that the current medical imaging device is a CT scanner is taken as an example. The cloud platform may classify the medical images and/or scan data of all the medical imaging devices connected to it for storage according to scanned portions of each scanned object. For example, the medical images and/or scan data of arms may be stored together, and the medical images and/or scan data of legs may be stored together. Then, if the current CT scanner wants to scan a certain portion of the object to be scanned, the cloud platform may perform matching on the classified and stored medical images and/or scan data according to information of anteroposterior and lateral films of the object to be scanned, so as to find, in the matched classification, the most similar medical image and/or scan data of the same scanned portion of other reference object.

Specifically, in an implementation of this step, the minimum distance between the medical images of two scanned objects may be calculated on the basis of the scanned portion classification by using the information of the medical images. The reference object whose medical image has the minimum distance from the medical image of the object to be scanned is the matching result in this step. In a case that the medical image of other reference object is stored, the minimum distance may be calculated directly. In a case that the data stored for the other reference object is scan data, the cloud platform may reconstruct the scan data into the medical image and then calculate the minimum distance.

In the calculation, a geometry change as shown in Equation (7) may be performed on the medical image of the object to be scanned. Then the medical image of the object to be scanned is matched with the medical images and/or scan data on the platform, so as to find, as the matching result, a medical image of other reference object which has the minimum distance from the medical image of the object to be scanned.

$$I'(i,j) = I(R(k_1 i + t_1, k_2 j + t_2)) \quad (7)$$

I denotes the medical image of the scanned portion of the object to be scanned. R(,) denotes a coordinate rotation transformation. For the medical images and/or scan data K stored on each cloud platform, Equation (8) is used to calculate the mutual information of K and I':

$$M(A, B) = -\sum_a P_A(a)\log_2 P_A(a) - \sum_a P_B(a)\log_2 P_B(a) + \sum_{a,b} P_{AB}(a,b)\log_2 P_{AB}(a,b) \quad (8)$$

$P_A(a)$ denotes the probability that the value of the pixel in the image I' is a, $P_B(a)$ denotes the probability that the value of the pixel in the image K is a, and $P_{AB}(a,b) = P_A(a) \cdot P_B(b)$.

Finally, the values of R (,) and $k_1$, $t_1$, $k_2$, $t_2$ are calculated, so that M (A, B) has the maximum value. The obtained value of M (A, B) is the distance between the image I and the image K. The reference object corresponding to the minimum distance among the obtained distances is chosen, and the medical image and/or scan data of the chosen reference object is used for the dose modulation of the scan to be performed on the object to be scanned by the current CT scanner. Therefore a lot of dose may be saved for the current scan of the current CT scanner.

Step 602: a parameter required by dose optimization of the object to be scanned is generated based on the medical image and/or scan data obtained by the matching, so that the current medical imaging device performs a dose-optimized scan on the object to be scanned base on the parameter.

In the present embodiment, the dose modulation plan for the object to be scanned may be made according to the medical image and/or scan data of other reference object. Thereby, for the current CT scanner, the optimal result of the scan performed on the object to be scanned may be acquired by using minimum dose. The generated parameter required by the dose optimization of the object to be scanned may be included in a dose modulation image, for example, the conventional medical image information such as dose information, reconstruction method, a reconstruction convolution kernel, layer thickness and/or reconstruction field for an object to be scanned. Therefore the current CT scanner may perform scanning and reconstruction on the object to be scanned according to those parameters, to obtain a most consistent image.

In this embodiment, the matched medical image and/or scan data may be returned directly to the current CT scanner for the doctor to refer to. Therefore, the doctor may have a brief overview of the image quality of the medical image before using the current CT scanner to scan, so as to judge whether the requirement of the diagnosis can be met. Moreover, the reference object found by the matching is very similar to the object to be scanned, thus a similar medical image of the object to be scanned may be previewed from the medical image of the reference object. Therefore, a reference is provided to the doctor about whether the solution of scanning the user to be scanned by the current CT scanner should be adjusted.

In a different application, orthographic projection may be directly performed on the medical image of the reference object found by the matching, to calculate attenuation information required by the dose modulation of the current CT scanner. The attenuation information is directly used for the dose modulation performed on the current scan of the user to be scanned by the current CT scanner. The process of performing orthographic projection on the medical image to obtain the attenuation information required by the dose modulation of the CT scanner is as follows. A circle angle of 360 degrees is divided into 360 parts. For each z position (generally, in a medical image obtained by the scanning of the CT scanner, the forward direction along a scan bed is defined as the z direction) and for each angle a (the angle is an angle of 1 degree after the angle of 360 degrees is divided into 360 parts), the orthographic projection is performed on the medical image of the reference object by using the projection geometry of the current CT (including a focus rotation radius and a channel angle, layer thickness). The obtained data of the orthogonal projection is stored in the current CT scanner. Thus, when the current CT scanner performs a scan subsequently, the result data of the orthogonal projection of the medical image of the reference object may be used for performing interpolation on the current scan position and the current scan angle. Thereby, the result of the interpolation may be used as the reference of the dose modulation of the current CT scanner for dose optimization.

In this embodiment, the medical image and/or scan data of the reference object most similar to the object to be scanned is found out from the medical images and/or scan data stored on the cloud platform classified according to the scanned portions, and the dose modulation plan of the object to be scanned may be made according to the medical image and/or scan data of the reference object, so that the optimal medical image and/or scan data may be acquired during the scanning of the current CT scanner by using the minimum dose. Furthermore, the medical image and/or scan data of the reference object may be shown directly to the doctor, so that the doctor may have a brief overview of the quality of the medical image and/or scan data before using the current CT scanner to scan, so as to judge whether the current scan of the current CT scanner can meet the requirement of the diagnosis.

Figure 7:
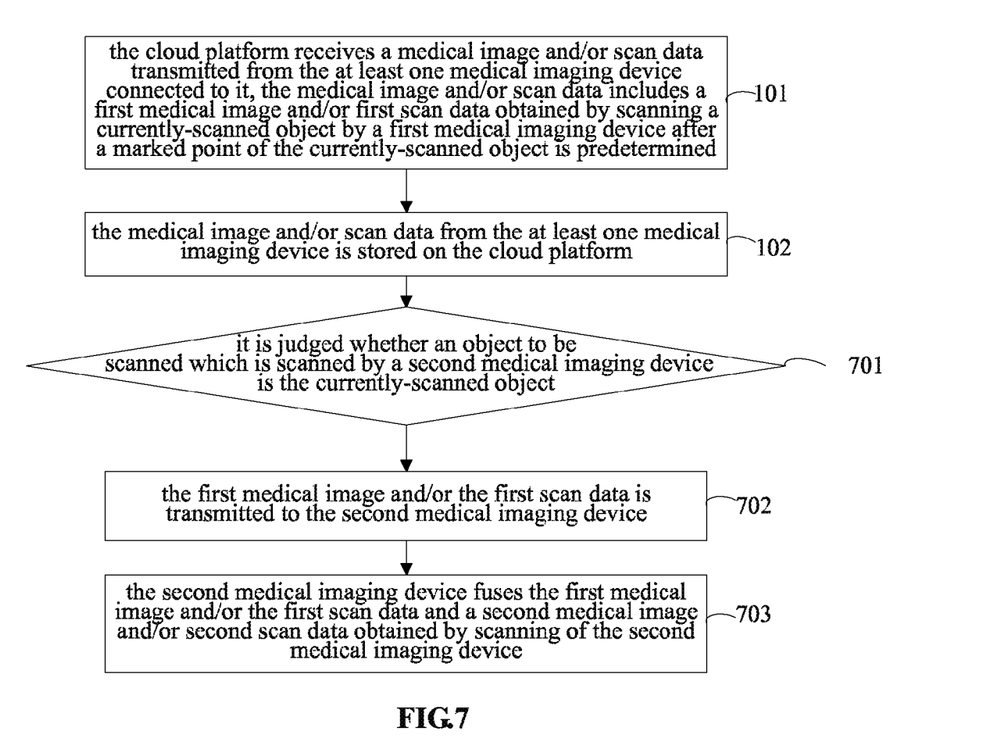
FIG. 7 is a flowchart of a fourth embodiment of the method according to the invention.

Referring to FIG. 7, a flowchart of a fourth embodiment of the method for sharing medical image data based on a cloud platform according to the invention is shown. The medical image and/or scan data includes: a first medical image and/or first scan data obtained by scanning a currently-scanned object by a first medical imaging device after a marked point of the currently-scanned object is predetermined; and the method further includes the following steps after Step 101 and Step 102.

Step 701: it is judged whether an object to be scanned which is scanned by a second medical imaging device is the currently-scanned object, and if it is, the process proceeds to Step 702.

In the embodiment, if an object to be scanned needs to be scanned by a medical imaging device, some marked points may be added in advance to the scanned portions of the object to be scanned. The marked point may be metal or other material. Since the medical imaging device is sensitive to metal, an apparent feature may appear on the medical image and/or scan data. When the same object to be scanned needs to be scanned by another medical imaging device, the cloud platform may automatically transmit the medical image and/or scan data of the last medical imaging device to the another medical imaging device, and automatic location of the medical image and/or scan data may be performed according to the marked point. Therefore, the fusion is more accurate without aligning the obtained medical images and/or scan data of the two medical imaging devices, so as to obtain an accurate fused image.

For example, the first medical imaging device is a CT scanner and the second medical imaging device is a PET. When the object to be scanned is scanned by the CT scanner, some markers are added in advance for location. Then, when the object to be scanned is scanned by the PET, the automatic location may be implemented on the PET by using the medical image and/or scan data of the CT scanner transmitted via the cloud platform. In implementation of this step, if the cloud platform detects that the object scanned by the PET is the same one as the object scanned by the CT scanner, the process proceeds to a subsequent step 702.

Step 702: the first medical image and/or the first scan data is transmitted to the second medical imaging device.

The cloud platform transmits the first medical image and/or the first scan data of the CT scanner to the PET.

In an implementation, it is assumed that the two terminals are a CT scanner and a PET, the marked points are metal, and the total number of the marked points is N, where N is a positive integer. The fusion process of the medical image of the CT scanner and the medical image of the PET is as follows.

Positions $P_1, Q_1$ of the N marked points are found out respectively in three-dimensional images $I_{CT}, I_{PBT}$ of the CT scanner and the PET by using an image threshold. Then A, p and K are found out, and the values of A, p and K lead to a minimum value of Equation (9), Equation (9) is as follows:

$$\sum_i (A * P_{K_i} + p - Q_i)^2 \qquad (9)$$

A is a 3×3 rotation matrix. p is a three-dimensional image point. K is any permutation and combination of $\{1 \ldots N\}$. K is any numerical value in the any permutation and combination. For example, it is assumed that N is 3 and K is $\{2,1,3\}$, then the value of $K_i$ is respectively 2,1,3, and $P_{K_i}$ is respectively $P_2$, $P_1$ and $P_3$.

Step 703: the second medical imaging device fuses the first medical image and/or the first scan data and a second medical image and/or second scan data obtained by scanning of the second medical imaging device.

After A, p and K are obtained, the fusion may be performed on the corresponding pixel points of the medical image $A*I_{CT}+p$ of the CT scanner and the medical image $I_{PBT}$ of the PET, so as to obtain a fused medical image.

In the embodiment, it can be understood that, if a medical image is stored on the cloud platform, the fusion may be performed directly; and if scan data is stored on the cloud platform, the scan data may be reconstructed into a medical image and then fused. In the embodiment, some markers or parameters are added on the object to be scanned during the scanning of the current CT scanner for location, and then when the object to be scanned is scanned by the PET, automatic location is implemented on the PET according to the medical image and/or scan data of the CT scanner transmitted via the cloud platform. Therefore, after the PET scan, the medical images of the CT scanner and the PET may be well fused, so that the two separated CT scanner and PET can achieve the scanning effect of a synthetic PET-CT device.

In a different application, the medical image and/or scan data obtained by scanning an object to be scanned by a medical imaging device may be used to improve the quality of a medical image and/or scan data of another medical imaging device. For example, in the embodiment, attenuation correction may be performed on the medical image and/or scan data of the PET according to the scan result of the CT scanner in a fusion way, thereby improving the uniformity of the PET image.

In practical applications, the cloud platform stores medical images and/or scan data of multiple medical imaging devices. Therefore, the cloud platform also correspondingly stores some relevant information of multiple scanned objects. The object to be scanned may store the medical image and/or scan data of himself/herself on an electronic device (a terminal device such as a wrist-watch or a smart phone), so that the object to be scanned may be queried on the electronic device. Moreover, information such as dose information of the object to be scanned may be uploaded to the cloud platform via the above-mentioned electronic device. Therefore, before the object to be scanned is scanned, the doctor can know the cumulative dose of the object to be scanned in a certain time period, so as to more reasonably make a plan for the current scan.

When the historical medical images and/or scan data of all the medical imaging devices are stored on the cloud platform, the historical medical images and/or scan data may be downloaded from the cloud platform as reference for scanning the current object to be scanned. Moreover, the historical medical image and/or scan data of an object to be scanned with the same scanned portion and the same case of illness may be downloaded as required, for reference by the doctor. Furthermore, matching of the medical image and/or scan data may be triggered automatically by the cloud platform so as to download a medical image and/or scan data of a scanned object with the same case of illness, for reference by the doctor. Furthermore, the doctor, after finishing the diagnosis of the scanned object (i.e., patient), may upload the medical image and/or scan data obtained by the medical imaging device and the diagnosis result to the cloud platform to be used as a part of the historical medical images and/or scan data.

Figure 8:
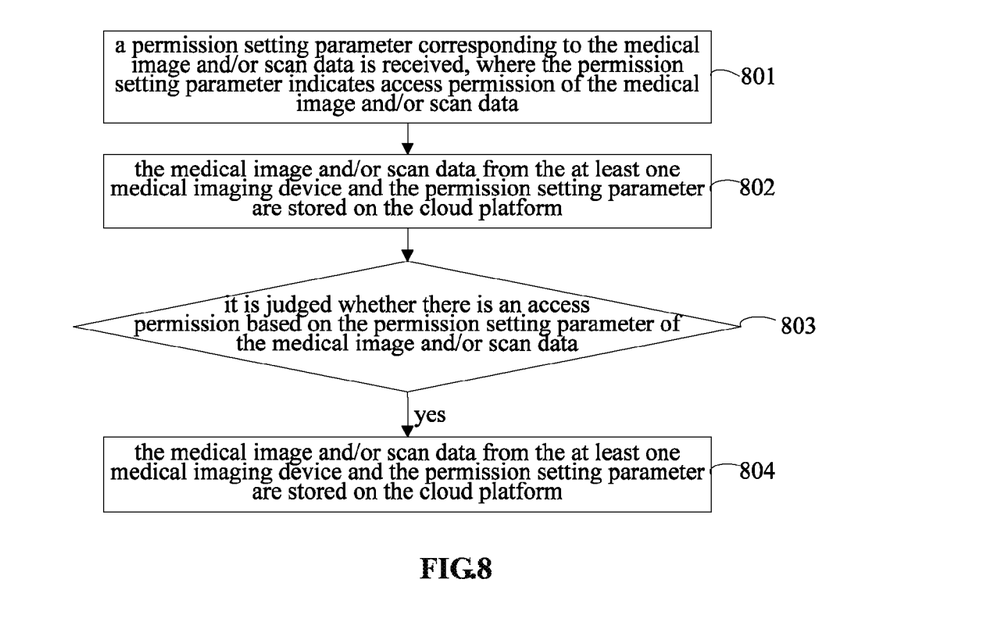
FIG. 8 is a flowchart of a fifth embodiment of the method according to the invention.

In order to ensure the security of the medical image and/or scan data of the scanned object, a flowchart of a fifth embodiment of the method for sharing medical image data based on a cloud platform according to the invention is shown in FIG. 8. During Step 101 in which a medical image and/or scan data is received, the method may further include the following steps.

Step 801: a permission setting parameter corresponding to the medical image and/or scan data is received, where the permission setting parameter indicates access permission of the medical image and/or scan data.

In this embodiment, the cloud platform, when receiving the medical image and/or scan data transmitted from the medical imaging device, may also receive a permission setting parameter corresponding to each medical image and/or scan data. The permission setting parameter may indicate the access permission of the medical image and/or scan data. For example, a certain medical image and/or scan data is allowed to be accessed and downloaded by all the persons, or is only allowed to be accessed and downloaded by some specific persons.

Step 802: the medical image and/or scan data of the at least one medical imaging device and the permission setting parameter are stored on the cloud platform.

The cloud platform stores the received medical image and/or scan data as well as the permission setting parameter.

Step 803: in response to a request of acquiring a medical image and/or scan data of a scanned object which is transmitted by an electronic device, it is judged whether there is an access permission based on the permission setting parameter of the medical image and/or scan data, and if there is an access permission, the process proceeds to Step 804.

If a user subsequently transmits, to the cloud platform via an electronic device, a request of acquiring a medical image and/or scan data of a certain scanned object, the cloud platform judges based on the permission setting parameter stored in Step 802 whether the user has the access permission of the medical image and/or scan data of the scanned object. If the user has the access permission, the process proceeds to Step 804. If the user does not have the access permission, the cloud platform may do nothing, or the cloud platform may return information that the user does not have the access permission to the user, and so on.

Step 804: the medical image and/or scan data is returned.

The cloud platform returns the corresponding medical image and/or scan data if the user has the access permission of a certain medical image and/or scan data, so as to ensure the security of the medical image and/or scan data. Therefore, it is ensured that other patient, doctor or hospital can access or use the medical image and/or scan data of the patient only if the patient grants an authorization, so as to well protect the privacy of the patient.

It can be understood that there are various ways for the patient to grant authorization. For example, when the patient has a medical examination in a hospital, the medical image and/or scan data stored on the cloud platform can not be directly displayed to a doctor. Instead, the patient generates a UKey or a short message or an email by specific software to grant the authorization to a doctor. The doctor can access the medical image and/or scan data of the patient after inserting the terminal of the UKey of the patient or receiving the authorization short message or email. In another example, when a patient registers in a certain hospital, the software of the cloud platform may automatically acquire authorization from the registration information of the patient, and a relevant doctor may have the access permission for a certain time period (the length of the time period may be set by the patient himself/herself). In this time period, the doctor can access the medical image and/or scan data of the patient on the cloud platform.

According to the above-mentioned description of the embodiments of the method, the skilled in the art can understand clearly that the invention may be implemented by using a software in conjunction with a necessary universal hardware platform or may be implemented in hardware, with the former being a more preferable embodiment. Based on the understanding, the essence of the technical solution of the invention or the part of the technical solution of the invention which contributes to the prior art may be embodied in a software production. The computer software production is stored in a storage medium and includes multiple instructions for making a computer device (which may be a personal computer, a server, or a network device) to perform all or part of steps in the embodiments of the method according to the invention. The above-mentioned storage medium includes various media capable of storing program code, such as a read only memory (ROM), a random access memory (RAM), a disk or a disc.

Figure 9:
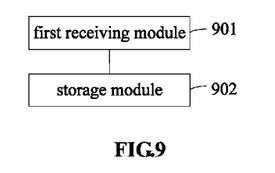
FIG. 9 is a structural schematic view of a first embodiment of a cloud platform according to the invention.

Corresponding to the above-mentioned embodiments of the method, a device for sharing medical image data based on a cloud platform is further provided according to an embodiment of the invention. Referring to FIG. 9, a structural schematic view of a first embodiment of a cloud platform for sharing medical image data is shown. The cloud platform is connected to at least one medical imaging device. The cloud platform may include:

a first receiving module 901 adapted for receiving a medical image and/or scan data transmitted from the at least one medical imaging device; and a storage module 902 adapted for storing, on the cloud platform, the medical image and/or the scan data from the at least one medical imaging device.

In the embodiment, each medical imaging device no longer stores the scan data and/or the medical image in its own storage space. Instead, each medical imaging device transmits the scan data and/or the medical image to the cloud platform connected to it, and the cloud platform stores the medical images and/or the scan data of all the medical imaging devices connected to it. In this way, when a certain medical imaging device needs to acquire the medical image and/or scan data of other medical imaging device, the certain medical imaging device may directly read the medical image and/or the scan data from the cloud platform connected to it. Thereby, the medical image and/or scan data sharing between all of the medical imaging devices connected to the cloud platform is achieved.

Figure 10:
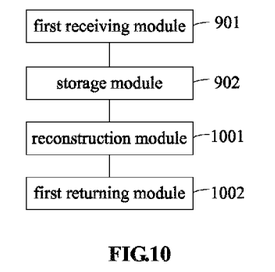
FIG. 10 is a structural schematic view of a second embodiment of the cloud platform according to the invention.

Referring to FIG. 10, a structural schematic view of a second embodiment of the cloud platform for sharing medical image data is shown. Besides the modules shown in FIG. 9, the cloud platform may further include:

a reconstruction module 1001 adapted for, in response to a medical image generation request from the current medical imaging device, reconstructing a corresponding medical image based on the scan data from the current medical imaging device.

Figure 11:
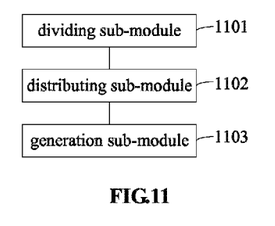
FIG. 11 is a structural schematic view of a reconstruction module 1001 in the second embodiment of the cloud platform according to the invention.

Referring to FIG. 11, the reconstruction module 1001 may include:

a dividing sub-module 1101 adapted for dividing the scan data from the current medical imaging device into multiple data sub-sets;

a distributing sub-module 1102 adapted for distributing the multiple data sub-sets to multiple compute nodes chosen according to a predetermined condition correspondingly, so as to trigger the multiple compute nodes to respectively calculate medical sub-images of the multiple data sub-sets, where the number of the data sub-sets consists with the number of the multiple compute nodes; and a generation sub-module 1103 adapted for generating a medical image corresponding to the scan data by using the medical sub-images of the multiple data sub-sets.

A first returning module 1002 is adapted for returning the medical image to the current medical imaging device.

In the embodiment, each medical imaging device may instruct the cloud platform to reconstruct the medical image. Therefore, the use cost of the medical imaging device may be reduced, the efficiency of the medical image reconstruction may be improved and the resource of the medical imaging device may be saved.

Figure 12:
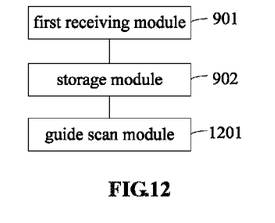
FIG. 12 is a structural schematic view of a third embodiment of the cloud platform according to the invention.

Referring to FIG. 12, a structural schematic view of a third embodiment of the cloud platform for sharing medical image data is shown. The cloud platform may include:

a guide scan module 1201 adapted for, in response to a guide scan request from a current medical imaging device, performing a guide scan of the current medical imaging device based on a stored medical image and/or scan data from other medical imaging device.

Figure 13:
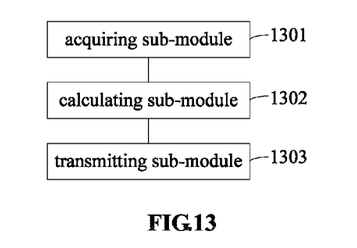
FIG. 13 is a structural schematic view of one example of the third embodiment of the cloud platform according to the invention.

The medical imaging device includes a device capable of measuring cardiac output and a computed tomography CT scanner. Referring to FIG. 13, the guide scan module 1201 may include:

an acquiring sub-module 1301 adapted for, in response to an operation of enhanced scan to be performed by a current CT scanner on an object to be scanned, acquiring, from the cloud platform, cardiac output of the object to be scanned which is obtained by using the device capable of measuring cardiac output;

a calculating sub-module 1302 adapted for calculating, based on the cardiac output, total amount and injection speed of contrast medium required by the enhanced scan to be performed on the object to be scanned; and a transmitting sub-module 1303 adapted for transmitting the total amount and injection speed of the contrast medium to the current CT scanner, so that the current CT scanner performs the enhanced scan on the object to be scanned.

In this specific application, the enhanced scan of the CT scanner is achieved by using the cardiac output obtained by scanning of other medical imaging device. The calculation result is more accurate since the total amount and injection speed of the contrast medium is obtained by referring the history result of the object to be scanned.

Figure 14:
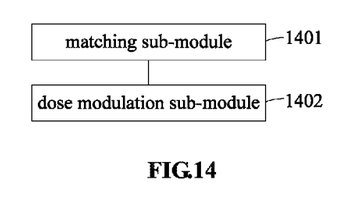
FIG. 14 is a structural schematic view of another example of the third embodiment of the cloud platform according to the invention.

Referring to FIG. 14, the guide scan module 1201 may include:

a matching sub-module 1401 adapted for, in response to a received medical image of a scanned portion of an object to be scanned which is transmitted from the current medical imaging device, performing matching on the cloud platform to obtain a stored medical image and/or scan data of a same scanned portion of other object; and a dose modulation sub-module 1402 adapted for generating, based on the medical image and/or scan data obtained by the matching, a parameter required by dose optimization of the object to be scanned, so that the current medical imaging device performs a dose-optimized scan on the object to be scanned base on the parameter.

In this embodiment, the medical image and/or scan data of the reference object most similar to the object to be scanned is found out from the medical images and/or scan data stored on the cloud platform that are classified according to the scanned portions. Moreover, the dose modulation plan of the object to be scanned may be made according to the medical image and/or scan data of the reference object, so that the optimal medical image and/or scan data may be acquired during the scanning of the current CT scanner by using the minimum dose.

Figure 15:
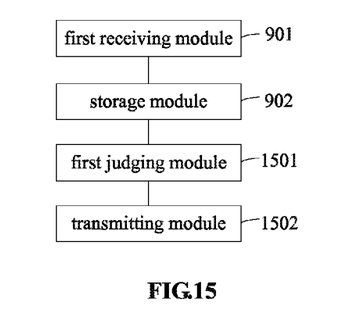
FIG. 15 is a structural schematic view of a fourth embodiment of the cloud to platform according to the invention.

Referring to FIG. 15, a structural frame view of a fourth embodiment of the cloud platform for sharing medical image data is shown. Besides the first receiving module 901 and the storage module 902, the cloud platform may further include:

a first judging module 1501 adapted for judging whether an object to be scanned which is scanned by a second medical imaging device is the currently-scanned object, and a transmitting module 1502 adapted for transmitting the first medical image and/or the first scan data to the second medical imaging device if the first judging module determines that the object to be scanned which is scanned by the second medical imaging device is the currently-scanned object, so that the second medical imaging device fuses the first medical image and/or the first scan data and a second medical image and/or second scan data obtained by scanning of the second medical imaging device.

In the embodiment, some markers or parameters are added on the object to be scanned during the scanning of the current CT scanner for location. Then when the object to be scanned is scanned by the PET, the automatic location is performed on the PET according to the medical image and/or scan data of the CT scanner transmitted via the cloud platform. Therefore, after the scanning of the PET, the medical images of the CT scanner and the PET may be well fused, and the two separated CT scanner and PET can achieve the scanning effect of a synthetic PET-CT device.

Figure 16:
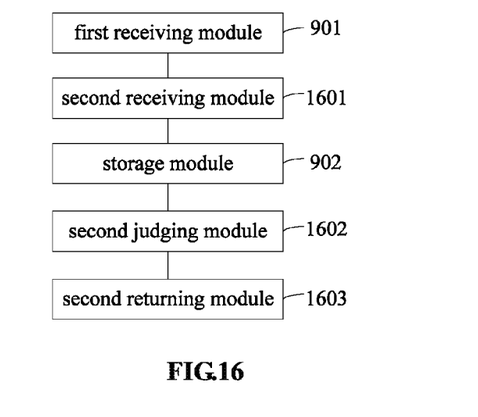
FIG. 16 is a structural schematic view of a fifth embodiment of the cloud platform according to the invention.

Referring to FIG. 16, a structural frame view of a fifth embodiment of the cloud platform for sharing medical image data is shown. Besides the first receiving module 901 and the storage module 902, the cloud platform may further include:

a second receiving module 1601 adapted for receiving a permission setting parameter corresponding to the medical image and/or scan data, where the permission setting parameter indicates access permission of the medical image and/or the scan data;

a second judging module 1602 adapted for, in response to a request of acquiring a medical image and/or scan data of a scanned object which is transmitted by an electronic device, judging whether there is an access permission based on the permission setting parameter of the medical image and/or scan data; and a second returning module 1603 adapted for returning the medical image and/or the scan data if the second judging module determines that there is an access permission.

In the embodiment, the security of the medical image and/or scan data is ensured. Therefore it is ensured that other patient, doctor or hospital can access or use the medical image and/or scan data of the patient only if the patient grants an authorization, so as to well protect the privacy of the patient.

Figure 17:
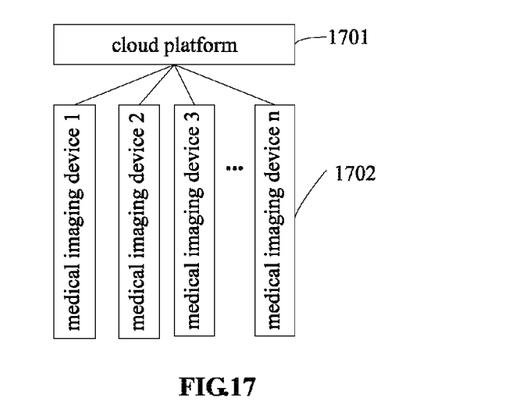
FIG. 17 is a structural schematic view of an embodiment of a system according to the invention.

As shown in FIG. 17, a system for sharing data is further provided according to an embodiment of the invention. The system may include a cloud platform 1701 and at least one medical imaging device 1702 connected to the cloud platform. The cloud platform 1701 may include: a first receiving module adapted for receiving a medical image and/or scan data transmitted from the at least one medical imaging device; and a storage module adapted for storing, on the cloud platform, the medical image and/or the scan data from the at least one medical imaging device.

It can be understood that the present invention may be applied to multiple general purpose or special purpose computing system environments or configurations, such as a personal computer, a server computer, a hand-held or portable device, a flat panel device, a multiprocessor systems, a microprocessor-based systems, a set-top box, a programmable consumer electronic device, a network PC, a mini-computer, a mainframe computer and a distributed computing environment including any of the above-mentioned systems or devices.

The invention may be described in a general context of a computer-executable instruction executed by a computer, such as a program module. Generally, the program module includes, for example, a routine, a program, an object, a component, or a data structure, which performs a particular task or implements a particular abstract data type. The invention may also be implemented in a distributed computing environment. In the distributed computing environment, a task is executed by a remote processing device connected via a communication network. In the distributed computing environment, the program module may be located in a local and remote computer storage medium including a storage device.

It should be noted that in the description, relationship terms such as "first" or "second" are only used to distinguish one entity or operation from another entity or operation, but does not necessarily require or imply that there is such actual relationship or order between these entities or operations. Moreover, the term "comprising", "including" or any other variant thereof intends to cover a non-exclusive inclusion, so that a process, method, article or device including a series of elements not only includes those elements but may also include other elements which are not explicitly listed, or may also include inherent elements of such process, method, article or device. If there is no more restriction, the element defined by the statement "includes a . . . " does not exclude that other same element is included in the process, method, article or device including said element.

The embodiments of the cloud platform and the system substantially correspond to the embodiments of the method. Therefore, relevant portions may refer to the corresponding description of the embodiments of the method. The above-described embodiments of the cloud platform and the system are merely illustrative. A unit described as a separated part may be or may not be physically separated. A part shown as a unit may be or may not be a physical unit, may be located in one place or may be distributed in multiple network units. A part or all of the modules may be chosen as required to achieve the purpose of the present embodiment. The skilled in the art may understood and implement the invention without any creative work.

Those described above are only embodiments of the present invention. It should be noted that, for the skilled in the art, improvements and modifications may also be made without departing from the principle of the invention. Those improvements and modifications should also be included in the scope of protection of the present invention.

The invention claimed is:

1. A method for sharing medical image data based on a cloud platform, the cloud platform being connected to at least one medical imaging device, the method comprising:
   receiving a medical image and/or scan data transmitted from the at least one medical imaging device; and
   storing, on the cloud platform, the medical image and/or the scan data from the at least one medical imaging device,
   wherein the method further comprises:
   in response to a guide request from a current medical imaging device, performing a guide for the current medical imaging device based on a stored medical image and/or scan data from other medical imaging device, and
   wherein the performing a guide for the current medical imaging device comprises:
   in response to a received medical image of a scanned portion of an object to be scanned which is transmitted from the current medical imaging device, performing matching on the cloud platform so as to obtain a stored medical image and/or scan data of a same scanned portion of other object; and
   generating, based on the medical image and/or the scan data obtained by the matching, a parameter required by dose optimization of the object to be scanned, so the current medical imaging device performs a dose-optimized scan on the object to be scanned base on the parameter.

2. The method according to claim 1, wherein, in a case that the scan data is transmitted from a current medical imaging device, the method further comprises:
in response to a medical image generation request from the current medical imaging device, reconstructing a corresponding medical image based on the scan data from the current medical imaging device.

3. The method according to claim 2, wherein the reconstructing a corresponding medical image based on the scan data from the current medical imaging device comprises:
dividing the scan data from the current medical imaging device into a plurality of data sub-sets;
distributing the plurality of data sub-sets to a plurality of compute nodes chosen according to a predetermined condition correspondingly, so as to trigger the plurality of compute nodes to respectively calculate medical sub-images of the plurality of data sub-sets, wherein the number of the data sub-sets consists with the number of the plurality of compute nodes; and
generating a medical image corresponding to the scan data by using the medical sub-images of the plurality of data sub-sets.

4. The method according to claim 3, further comprising:
returning the medical image to the current medical imaging device.

5. The method according to claim 2, further comprising:
returning the medical image to the current medical imaging device.

6. The method according to claim 1, wherein the medical imaging device comprises a device capable of measuring cardiac output and a computed tomography CT scanner, and the performing a guide for the current medical imaging device comprises:
in response to an operation of enhanced scan to be performed by a current CT scanner on an object to be scanned, acquiring, from the cloud platform, cardiac output of the object to be scanned which is obtained by using the device capable of measuring cardiac output;
calculating, based on the cardiac output, total amount and injection speed of contrast medium required by the enhanced scan to be performed on the object to be scanned; and
transmitting the total amount and injection speed of the contrast medium to the current CT scanner, so the current CT scanner performs enhanced scan on the object to be scanned.

7. The method according to claim 1, wherein the medical image and/or the scan data comprises: a first medical image and/or first scan data obtained by scanning a currently-scanned object by a first medical imaging device after a marked point of the currently-scanned object is predetermined; and the method further comprises:
judging whether an object to be scanned which is scanned by a second medical imaging device is the currently-scanned object, and if it is, transmitting the first medical image and/or the first scan data to the second medical imaging device, so the second medical imaging device fuses the first medical image and/or the first scan data and a second medical image and/or second scan data obtained by scanning of the second medical imaging device.

8. The method according to claim 1, further comprising:
during the receiving a medical image and/or scan data transmitted from the at least one medical imaging device,
receiving a permission setting parameter corresponding to the medical image and/or the scan data, wherein the permission setting parameter indicates access permission of the medical image and/or the scan data;
and the method further comprises: after the storing, on the cloud platform, the medical image and/or the scan data from the at least one medical imaging device,
in response to a request of acquiring a medical image and/or scan data of a scanned object which is transmitted by an electronic device, judging whether there is an access permission based on the permission setting parameter of the medical image and/or the scan data, and if it is, returning the medical image and/or the scan data.

9. A cloud platform for sharing medical image data, the cloud platform being connected to at least one medical imaging device, and the cloud platform comprising a processor and a non-transitory processor-readable medium having processor-executable instructions stored thereon that, when executed by the processor, cause the cloud platform to:
receive a medical image and/or scan data transmitted from the at least one medical imaging device; and
store, on the cloud platform, the medical image and/or the scan data from the at least one medical imaging device,
wherein the instructions further cause the cloud platform to:
in response to a guide request from a current medical imaging device, perform a guide for the current medical imaging device based on a stored medical image and/or scan data from other medical imaging device, and
wherein the performing a guide for the current medical imaging device based on a stored medical image and/or scan data from other medical imaging device comprises:
in response to a received medical image of a scanned portion of an object to be scanned which is transmitted from the current medical imaging device, performing matching on the cloud platform so as to obtain a stored medical image and/or scan data of a same scanned portion of other object; and
generating, based on the medical image and/or the scan data obtained by the matching, a parameter required by dose optimization of the object to be scanned, so the current medical imaging device performs a dose-optimized scan on the object to be scanned base on the parameter.

10. The cloud platform according to claim 9, wherein the instructions further cause the cloud platform to:
in response to a medical image generation request from a current medical imaging device, reconstruct a corresponding medical image based on the scan data from the current medical imaging device.

11. The cloud platform according to claim 10, wherein reconstructing a corresponding medical image based on the scan data from the current medical imaging device comprises:
dividing the scan data from the current medical imaging device into a plurality of data sub-sets;
distributing the plurality of data sub-sets to a plurality of compute nodes chosen according to a predetermined condition correspondingly, so as to trigger the plurality of compute nodes to respectively calculate medical sub-images of the plurality of data sub-sets, wherein the number of the data sub-sets consists with the number of the plurality of compute nodes; and generating a medical image corresponding to the scan data by using the medical sub-images of the plurality of data sub-sets.

12. The cloud platform according to claim 10, wherein the instructions further cause the cloud platform to:
return the medical image to the current medical imaging device.

13. The cloud platform according to claim 9, wherein the medical imaging device comprises a device capable of measuring cardiac output and a computed tomography CT scanner, and performing a guide for the current medical imaging device based on a stored medical image and/or scan data from other medical imaging device comprises:
in response to an operation of enhanced scan to be performed by a current CT scanner on an object to be scanned, acquiring, from the cloud platform, cardiac output of the object to be scanned which is obtained by using the device capable of measuring cardiac output;
calculating, based on the cardiac output, total amount and injection speed of contrast medium required by the enhanced scan to be performed on the object to be scanned; and
transmitting the total amount and injection speed of the contrast medium to the current CT scanner, so that the current CT scanner performs enhanced scan on the object to be scanned.

14. The cloud platform according to claim 9, wherein the medical image and/or the scan data comprises: a first medical image and/or first scan data obtained by scanning a currently-scanned object by a first medical imaging device after a marked point of the currently-scanned object is predetermined; and the instructions further cause the cloud platform to:
judge whether an object to be scanned which is scanned by a second medical imaging device is the currently-scanned object, and
transmit the first medical image and/or the first scan data to the second medical imaging device if it is determined that the object to be scanned which is scanned by the second medical imaging device is the currently-scanned object, so the second medical imaging device fuses the first medical image and/or the first scan data and a second medical image and/or second scan data obtained by scanning of the second medical imaging device.

15. The cloud platform according to claim 9, wherein the instructions further cause the cloud platform to:
receive a permission setting parameter corresponding to the medical image and/or the scan data, wherein the permission setting parameter indicates access permission of the medical image and/or the scan data;
in response to a request of acquiring a medical image and/or scan data of a scanned object transmitted by an electronic device, judge whether there is an access permission based on the permission setting parameter of the medical image and/or the scan data; and
return the medical image and/or the scan data if it is determined that there is an access permission.

16. A system for sharing data, comprising a cloud platform and at least one medical imaging device connected to the cloud platform, wherein the cloud platform comprises a processor and a non-transitory processor-readable medium having processor-executable instructions stored thereon that, when executed by the processor, cause the cloud platform to:
receive a medical image and/or scan data transmitted from the at least one medical imaging device; and
store, on the cloud platform, the medical image and/or the scan data from the at least one medical imaging device,
wherein the instructions further cause the cloud platform to:
in response to a guide request from a current medical imaging device, perform a guide for the current medical imaging device based on a stored medical image and/or scan data from other medical imaging device, and
wherein the performing a guide for the current medical imaging device based on a stored medical image and/or scan data from other medical imaging device comprises:
in response to a received medical image of a scanned portion of an object to be scanned which is transmitted from the current medical imaging device, performing matching on the cloud platform so as to obtain a stored medical image and/or scan data of a same scanned portion of other object; and
generating, based on the medical image and/or the scan data obtained by the matching, a parameter required by dose optimization of the object to be scanned, so the current medical imaging device performs a dose-optimized scan on the object to be scanned base on the parameter.

* * * * *